United States Patent
Bachmann et al.

(10) Patent No.: US 6,689,733 B1
(45) Date of Patent: *Feb. 10, 2004

(54) MANGANESE COMPLEXES OF SALEN LIGANDS AND THE USE THEREOF

(75) Inventors: Frank Bachmann, Freiburg (DE);
Rachel Allemann, Saint-Louis (FR);
Josef Dannacher, Basel (CH);
Marie-Josée Dubs, Wittersdorf (FR);
Cornelia Makowka, Laufenburg (DE);
Grit Richter, Neuenburg (DE);
Gunther Schlingloff, Riehen (CH);
Peter Weingartner, Diegten (CH);
Menno Hazenkamp, Basel (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/914,911

(22) PCT Filed: Feb. 24, 2000

(86) PCT No.: PCT/EP00/01508
§ 371 (c)(1),
(2), (4) Date: Sep. 5, 2001

(87) PCT Pub. No.: WO00/53574
PCT Pub. Date: Sep. 14, 2000

(30) Foreign Application Priority Data

Mar. 8, 1999 (CH) ................................ 427/99
Oct. 5, 1999 (CH) ............................... 1816/99

(51) Int. Cl.[7] ............................ C11D 3/20; C11D 3/26; C11D 3/39; C11D 3/395
(52) U.S. Cl. .................. 510/376; 510/220; 510/221; 510/224; 510/372; 510/378; 252/186.29; 252/186.33; 502/200; 502/324

(58) Field of Search .................... 510/220, 221, 510/224, 372, 376, 378; 252/186.29, 186.33; 8/111, 137; 502/200, 324

(56) References Cited

U.S. PATENT DOCUMENTS

| | | | | |
|---|---|---|---|---|
| 5,733,341 A | * | 3/1998 | Eckhardt et al. | 8/111 |
| 5,744,620 A | | 4/1998 | Hsiao et al. | 549/533 |
| 6,306,808 B1 | * | 10/2001 | Hazenkamp et al. | 510/224 |
| 6,387,863 B1 | * | 5/2002 | Hazemkamp et al. | 510/311 |
| 6,413,926 B2 | * | 7/2002 | Bachmann et al. | 510/311 |
| 2001/0003737 A1 | * | 6/2001 | Reinehr et al. | 510/376 |

FOREIGN PATENT DOCUMENTS

| | | |
|---|---|---|
| EP | 630964 | * 12/1994 |
| EP | 0693550 | 1/1996 |
| EP | 0902083 | 3/1999 |
| EP | 0955289 | 11/1999 |
| GB | 2296015 | 6/1996 |
| WO | 96/40148 | 12/1996 |
| WO | 97/07192 | 2/1997 |

OTHER PUBLICATIONS

S. Srinivasan et al., J. Am. Chem. Soc. (1986), vol. 108, No. 9, pp. 2309–2320.
F. Sakamoto et al., Chem. Lett. (1998), (11), pp 1127–1128.
English abstract for JP 2000054256, Feb. 22, 2000.
T. Tanaka et al., Bull Chem. Soc. Jpn., vol. 70, pp. 615–629, (1997).

* cited by examiner

Primary Examiner—Gregory Delcotto
(74) Attorney, Agent, or Firm—Kevin T. Mansfield

(57) ABSTRACT

The present invention relates to novel manganese complexes of salen ligands and the use thereof as catalysts that enhance the action of peroxy compounds in washing, cleaning, and disinfecting processes.

12 Claims, No Drawings

MANGANESE COMPLEXES OF SALEN LIGANDS AND THE USE THEREOF

The present invention relates to novel manganese complexes of salen ligands and to the use thereof as catalysts that enhance the action of peroxy compounds in washing, cleaning and disinfecting processes. The invention furthermore relates to formulations used in such processes that comprise the manganese complexes and peroxy compounds, and also to the novel ligands and to processes for the preparation thereof.

A number of manganese complexes of the salen type are already known to be suitable catalysts for oxidations that use peroxy compounds, especially within the context of washing procedures. Also, certain other manganese complexes have already been described as having a pronounced bleaching action on dirt and dyes in washing liquors. There is nevertheless still a need for further compounds having improved action and/or a broader field of application, but such compounds should not cause any appreciable damage to fibres or colours when used on textile material.

It has now been found that certain novel manganese complexes of the salen type as catalysts largely meet the required conditions. They enhance the action of peroxy compounds in a very wide variety of applications, substantially without damage occurring to fibres or colours. Surprisingly, when the manganese complexes according to the invention are employed in aqueous solution together with peroxy compounds, the enhanceed action occurs in the following applications:

a) the bleaching of stains or soiled areas on textile material within the context of a washing procedure,
b) the inhibition of migrating dyes being redeposited when textile material is washed,
c) the cleaning of hard surfaces, especially crockery or glass,
d) the cleaning of hard surfaces, especially glazed tiles or floor tiles, especially for the removal of stains that have formed as a result of the action of molds (mold stains), and
e) the use of washing and cleaning solutions that have an antibacterial activity.

The present invention accordingly relates to compounds of formula

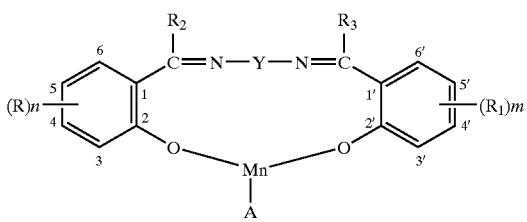

(1), wherein
n is 0, 1 or 2,
m is 1 or 2,
A is an anion;
Y is a linear or branched alkylene radical of formula —[C($R_5$)$_2$]$_r$— wherein r is an integer of from 1 to 8 and the $R_5$ radicals are each independently of the others hydrogen or $C_1$–$C_4$alkyl; —CX=CX— wherein X is cyano, linear or branched $C_1$–$C_8$alkyl or di(linear or branched $C_1$–$C_8$alkyl)amino; —(CH$_2$)$_q$—NR$_4$—(CH$_2$)$_q$— wherein $R_4$ is hydrogen or $C_1$–$C_4$alkyl and q is 1, 2, 3 or 4; or a 1,2-cyclohexylene radical of formula:

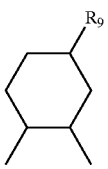

or a 1,2-aryl radical of formula

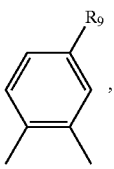

wherein $R_9$ is hydrogen, $SO_3H$, $CH_2OH$ or $CH_2NH_2$,
R and $R_1$ are each independently of the other nitro, $NR_6R_7$ wherein $R_6$ is hydrogen or linear or branched $C_1$–$C_{12}$alkyl and $R_7$ is linear or branched $C_1$–$C_{12}$alkyl, with the proviso that $R_6$ and $R_7$ in the groups $NR_6R_7$ are not identical, or —CH$_2$—N$^\oplus$R$_4$R$_6$R$_7$ or —N$^\oplus$R$_4$R$_6$R$_7$ wherein $R_4$, $R_6$ and $R_7$ are as defined above,
$R_2$ and $R_3$ are each independently of the other hydrogen, linear or branched $C_1$–$C_4$alkyl, unsubstituted aryl, or aryl substituted by cyano; by halogen; by $OR_5$ or $COOR_5$ wherein $R_5$ is hydrogen or linear or branched $C_1$–$C_4$alkyl; by nitro; by linear or branched $C_1$–$C_8$alkyl; by $NHR_6$ or $NR_6R_7$ wherein $R_6$ and $R_7$ are identical or different and are each linear or branched $C_1$–$C_{12}$alkyl; by linear or branched $C_1$–$C_8$alkyl-$R_8$ wherein $R_8$ is a radical $OR_5$, $COOR_5$ or $NR_6R_7$ as defined above or is $NH_2$; or by —N$^\oplus$R$_4$R$_6$R$_7$ wherein $R_4$, $R_6$ and $R_7$ are as defined above,
and, when n and m are each 1, $R_2$ and $R_3$ are each hydrogen and Y is unsubstituted 1,2-cyclohexylene, R and $R_1$ are not each nitro in the 5- and 5'-position, respectively, and, when n and m are each 1, $R_2$ and $R_3$ are each hydrogen and Y is unsubstituted 1,2-ethylene, R and $R_1$ are not each N$^\oplus$(CH$_3$)(C$_2$H$_5$)$_2$ in the 4- and 4'-position, respectively.

In compounds of formula (1) in which n is 2, the radicals R may have identical or different meanings. The same applies to compounds of formula (1) in which m is 2 in respect of the radicals $R_1$.

When Y is a 1,2-cyclohexylene radical, that radical may be in either of its stereoisomeric cis/trans forms.

Preferably, Y is a cyclohexylene radical, a radical of formula (CH$_2$)$_r$— wherein r is an integer of from 1 to 8, or a radical of formula —C($R_5$)$_2$—(CH$_2$)$_p$—C($R_5$)$_2$— wherein p is an integer of from 0 to 6 and $R_5$ is hydrogen or $C_1$–$C_4$alkyl.

In especially preferred compounds of formula (1), Y is a cyclohexylene radical, a radical of formula —(CH$_2$)$_r$— wherein r is an integer of from 1 to 4, or a radical of formula —(CR$_5$)$_2$—(CR$_5$)$_2$— wherein the $R_5$ radicals are each independently of the others hydrogen or methyl.

Halogen is preferably chlorine, bromine or fluorine, chlorine being especially preferred.

When n or m is 1, the groups R and $R_1$ are preferably in the 4- or 5-position of the respective benzene ring.

When $R_6$ or $R_7$ is an alkyl radical, the alkyl group may be straight-chain or branched. Preferably, the alkyl group contains from 1 to 8, especially from 1 to 4, and more especially from 1 to 3, carbon atoms.

Preferably, the radicals R and $R_1$ are each nitro, $NR_6R_7$ wherein $R_6$ and $R_7$ are each $C_1$–$C_4$alkyl, with the proviso that $R_6$ and $R_7$ are not identical, or —$N^{\oplus}R_4R_6R_7$ wherein $R_4$, $R_6$ and $R_7$ are each $C_1$–$C_4$alkyl.

The radicals $R_2$ and $R_3$ are especially hydrogen, methyl, ethyl, or unsubstituted phenyl.

Aryl is, for example, naphthyl or, especially, phenyl.

Suitable anions include, for example, halide, for example chloride, bromide or iodide, perchlorate, sulfate, nitrate, hydroxide, $BF_4^-$, $PF_6^-$, carboxylate, acetate, tosylate and triflate. Of those, preference is given to chloride, bromide, iodide and acetate.

The compounds of formula (1) are prepared, for example, in a manner known per se from the corresponding ligands and a manganese compound. Preparation processes of that kind are described, for example, in U.S. Pat. Nos. 5,281,578 and 4,066,459.

The ligands of formula

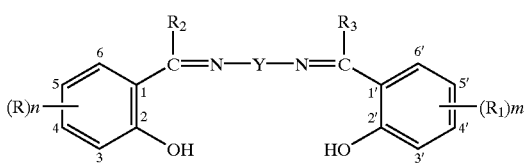

(2)

wherein R, $R_1$, $R_2$, $R_3$, Y, n and m are as defined for formula (1) are likewise novel. They are prepared in a manner known per se, for example by reacting a diamine of formula $H_2N$—Y—$NH_2$ first of all with an aldehyde or ketone of formula

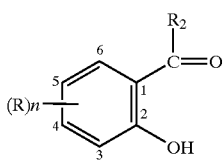

(3)

and then with an aldehyde or ketone of formula

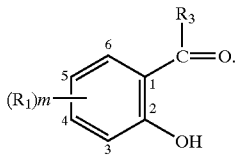

(4)

In formulae (3) and (4), R, $R_1$, $R_2$, $R_3$, n and m are as defined for formula (1). When, in the compounds of formula (2), $(R)_n$ has the same meaning as $(R_1)_m$ and $R_2$ has the same meaning as $R_3$ then, for the synthesis of compounds of formula (2), one mol of a diamine of formula $H_2N$—Y—$NH_2$ is reacted with two mols of an aldehyde or ketone of formula (3).

The diamines of formula $H_2N$—Y—$NH_2$ and the aldehydes or ketones of formula (3) and (4) are known or can be prepared in a manner known per se.

The compounds of formula (1) are used as catalysts for oxidations using peroxy compounds, for example for bleaching textile material, without causing appreciable damage to fibres and colours.

The present invention accordingly further relates to a washing and cleaning process which comprises adding to the liquor, which comprises a peroxide-containing washing and cleaning agent, from 0.1 to 200 μmol of one or more compounds of formula (1) per liter of washing liquor.

The present invention relates also to a method of inhibiting the redeposition of migrating dyes present in a washing liquor, which comprises adding to the washing liquor, which comprises a peroxide-containing washing agent, from 0.5 to 150 mg, preferably from 1.5 to 75 mg, especially from 7.5 to 40 mg, of one or more compounds of formula (1) per liter of washing liquor.

The present invention relates furthermore to a washing agent containing

I) from 5 to 90%, preferably from 5 to 70%, A) of an anionic surfactant and/or B) of a non-ionic surfactant, II) from 5 to 70%, preferably from 5 to 50%, especially from 5 to 40%, C) of a builder substance, III) from 0.1 to 30%, preferably from 1 to 12%, D) of a peroxide and IV) from 0.005 to 2%, preferably from 0.02 to 1%, especially from 0.1 to 0.5%, E) of a compound of the above-defined formula (1), the percentages in each case being percentages by weight, based on the total weight of the washing agent.

The washing agent may be in solid or liquid form, for example in the form of a liquid, non-aqueous washing agent containing not more that 5%, preferably from 0 to 1%, by weight of water, and may comprise as base a suspension of a builder substance in a non-ionic surfactant, for example as described in GB-A-2 158 454.

The washing agent is preferably, however, in the form of a powder or granules.

The powder or granules can be prepared, for example, by first preparing a starting powder by spray-drying an aqueous suspension comprising all of the above-listed components with the exception of components D) and E), and then adding the dry components D) and E) and mixing everything together.

It is also possible to add component E) to an aqueous suspension comprising components A), B) and C), then subject the mixture to spray-drying and subsequently mix component D) with the dry mass.

It is furthermore possible to start with an aqueous suspension that comprises components A) and C) but not component B) or only a proportion of component B). The suspension is spray-dried and then component E) is mixed with component B) and added, and subsequently component D) is admixed dry.

The anionic surfactant A) may be, for example, a sulfate, sulfonate or carboxylate surfactant or a mixture of such surfactants.

Preferred sulfates are those having from 12 to 22 carbon atoms in the alkyl radical, if desired in combination with alkylethoxysulfates in which the alkyl radical contains from 10 to 20 carbon atoms.

Preferred sulfonates include, for example, alkylbenzenesulfonates having from 9 to 15 carbon atoms in the alkyl radical.

The cation in the anionic surfactants is preferably an alkali metal cation, especially sodium.

Preferred carboxylates are alkali metal sarcosinates of formula R—CO—$N(R^1)$—$CH_2COOM^1$, wherein R is alkyl or alkenyl having from 8 to 18 carbon atoms in the alkyl or alkenyl radical, $R^1$ is $C_1$–$C_4$alkyl and $M^1$ is an alkali metal.

The non-ionic surfactant B) may be, for example, a condensation product of from 3 to 8 mols of ethylene oxide with 1 mol of primary alcohol that contains from 9 to 15 carbon atoms.

Suitable builder substances C) include, e.g., alkali metal phosphates, especially tripolyphosphates, carbonates or bicarbonates, especially the sodium salts thereof, silicates, aluminium silicates, polycarboxylates, polycarboxylic acids, organic phosphonates, aminoalkylenepoly (alkylenephosphonates) and mixtures of such compounds.

Silicates that are especially suitable are sodium salts of crystalline layer silicates of formula $NaHSi_tO_{2t+1} \cdot pH_2O$ or $Na_2Si_tO_{2t+1} \cdot pH_2O$, wherein t is a number from 1.9 to 4 and p is a number from 0 to 20.

Of the aluminium silicates, preference is given to those obtainable commercially under the names zeolite A, B, X and HS and to mixtures that comprise two or more of those components.

Of the polycarboxylates, preference is given to the polyhydroxycarboxylates, especially citrates, and acrylates and also copolymers thereof with maleic anhydride.

Preferred polycarboxylic acids are nitrilotriacetic acid, ethylenediaminetetraacetic acid and ethylenediamine disuccinate both in racemic form and the enantiomerically pure S,S-form.

Especially suitable phosphonates or aminoalkylenepoly (alkylenephosphonates) include alkali metal salts of 1-hydroxyethane-1,1-diphosphonic acid, nitrilo-tris (methylenephosphonic acid), ethylenediaminetetramethylenephosphonic acid and diethylenetriaminepentamethylenephosphonic acid.

Suitable peroxide components D) include, for example, the organic and inorganic peroxides known in the literature and available commercially that bleach textile materials at conventional washing temperatures, for example at from 10 to 95° C.

The organic peroxides are, for example, mono- or polyperoxides, especially organic peracids or salts thereof, such as phthalimidoperoxycaproic acid, peroxybenzoic acid, diperoxydodecanedioic acid, diperoxynonanedioic acid, diperoxydecanedioic acid, diperoxyphthalic acid or salts thereof.

Preference is given, however, to the use of inorganic peroxides, such as, for example, persulfates, perborates, percarbonates and/or persilicates. It will be understood that it is also possible to use mixtures of inorganic and/or organic peroxides. The peroxides can be present in various crystalline forms and with various water contents, and they can also be used together with other inorganic or organic compounds for the purpose of improving their storage stability.

The addition of the peroxides to the washing agent is carried out preferably by mixing the components together, for example using a screw metering system and/or a fluidized bed mixer.

The washing agent may comprise, in addition to the combination according to the invention, one or more optical brighteners, for example from the group comprising bistriazinylamino-stilbenedisulfonic acid, bistdazolylstilbenedisulfonic acid, bisstyrylbiphenyl or bisbenzofuranylbiphenyl, a bisbenzoxalyl derivative, bisbenzimidazolyl derivative, coumarin derivative or a pyrazoline derivative.

The washing agents may furthermore comprise suspending agents for dirt, for example sodium carboxymethylcellulose, pH regulators, e.g. alkali metal or alkaline earth metal silicates, foam regulators, e.g. soap, salts for regulating the spray-drying and the granulating properties, e.g. sodium sulfate, perfumes and, optionally, antistatic agents and softeners, enzymes, such as amylase, bleaching agents, pigments and/or toning agents. It will be understood that such components must be stable with respect to the bleaching agent used.

Further preferred additives to the washing agents according to the invention are polymers that, when textile materials are being washed, inhibit staining caused by dyes in the washing liquor that have been released from the textile materials under the washing conditions. Such polymers are preferably polyvinylpyrrolidones which, as appropriate, may have been modified by the incorporation of anionic or cationic substituents, especially those having a molecular weight in the range from 5000 to 60 000, more especially from 10 000 to 50 000. Such polymers are used preferably in an amount of from 0.05 to 5% by weight, especially from 0.2 to 1.7% by weight, based on the total weight of the washing agent.

In addition, the washing agents according to the invention may also comprise so-called perborate activators, such as, for example, TAED or TAGU. Preference is given to TAED, which is preferably used in an amount of from 0.05 to 5% by weight, especially from 0.2 to 1.7% by weight, based on the total weight of the washing agent.

Surprisingly, the manganese complexes of formula (1) also have a markedly improved bleach-catalyzing action on coloured stains on hard surfaces. The addition of such complexes in catalytic amounts to a dishwashing agent that comprises a peroxy compound and optionally TAED (N,N,N',N'-tetraacetylethylenediamine) results in the substantial removal of tea stains from porcelain at 45° C. in automatic dishwashers. This is the case even when hard water is used, it being known that tea deposits are more difficult to remove in hard water than in soft water.

The invention accordingly relates also to the use of manganese complexes of formula (1) as catalysts for reactions with peroxy compounds in cleaning solutions for hard surfaces, especially for crockery.

The invention relates furthermore to cleaning agents for hard surfaces, especially cleaning agents for crockery and, among such agents, preferably those for use in cleaning processes carried out by machine, which agents comprise one of the above-described compounds of formula (1) as bleach catalyst, and to a method of cleaning hard surfaces, especially crockery, using such a bleach catalyst.

The manganese complexes of formula (1) according to the invention are furthermore excellently suitable for cleaning hard surfaces, especially glazed tiles or floor tiles, especially for the removal of stains that have formed as a result of the action of molds ("mold stains"). Such stains frequently occur in the joints between glazed tiles. The joints may consist, for example, of cement-containing and/or gypsum-containing material, or of polymers, for example silicone.

The invention accordingly relates also to the use of manganese complexes of formula (1) as catalysts for reactions with peroxy compounds in cleaning solutions for glazed tiles and floor tiles, or the joints between such tiles, and to the cleaning solutions used for that purpose comprising a manganese complex of formula (1) and a peroxide and optionally further additives, such as, for example, surfactants.

Used together with peroxy compounds, the manganese complexes of formula (1) according to the invention furthermore exhibit excellent antibacterial activity. The invention relates also to the use of the manganese complexes of formula (1) according to the invention to kill bacteria or to provide protection against attack by bacteria.

The following Examples serve to illustrate the invention without the invention being limited thereto. Parts and percentages relate to weight, unless specified otherwise. Preparation of the ligands is expediently carried out under an argon atmosphere.

EXAMPLE 1

N,N'-Bis(4-trimethylammoniumsalicylidene)-1,2-ethylenediamine dihydrobromide

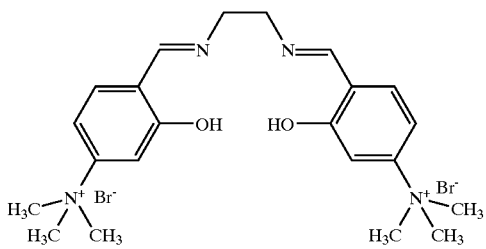

55 mg (0.915 mmol) of ethylenediamine are added dropwise, at 50° C., to a suspension of 500 mg (1.92 mmol) of 4-formyl-3-hydroxyphenyltrimethylammonium bromide [directions for synthesis: M. Ando, S. Emoto, Bull. Chem. Soc. Jpn., Vol. 42 (9) 2624 (1969)] in 2 ml of ethanol. The reaction mixture is maintained at 80° C. for 4 hours. After cooling to room temperature, the precipitate formed is filtered off, washed with a small amount of cold ethanol and dried to constant weight under a high vacuum at 40° C.

Yield: 390 mg (78%), yellowish solid. $^{13}$C NMR (DMSO-$d_6$) δ=57.1 (NCH$_3$), 58.4 (NCH$_2$), 110.6, 134.2 (tert. aryl-C), 119.7, 150.9, 163.7 (quat. aryl-C), 167.0 (C=N).

EXAMPLE 2

N,N'-Bis(5-trimethylammoniumsalicylidene)-1,2-ethylenediamine dihydrobromide

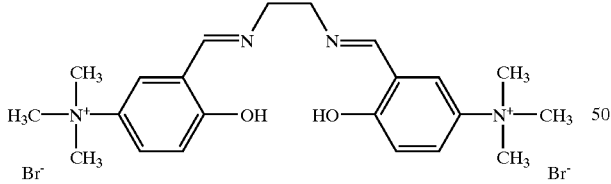

Synthesis and working up are carried out as in Example 1, starting from 500 mg (1.92 mmol) of 3-formyl4-hydroxyphenyltrimethylammonium bromide [directions for synthesis: M. Ando and S. Emoto, Bull. Chem. Soc. Jpn., Vol. 51 (8) 2433 (1978)].

Yield: 492 mg (99%), yellowish solid. $^{13}$C NMR (DMSO-$d_6$) δ=57.3 (NCH$_3$), 58.2 (NCH$_2$), 119.7, 124.5, 125.7 (tert. aryl-C), 118.2, 138.1, 163.6 (quat. aryl-C), 166.8 (C=N).

EXAMPLE 3

(R,R)-N,N'-Bis(5-trimethylammoniumsalicylidene)-1,2-cyclohexanediamine dihydrobromide

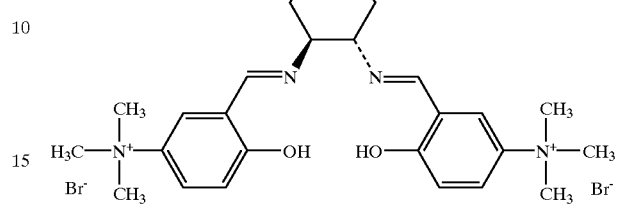

Synthesis and working up are carried out as in Example 1, starting from 500 mg (1.92 mmol) of 3-formyl4-hydroxyphenyltrimethylammonium bromide and 0.105 g (0.915 mmol) of trans-1,2-diaminocyclohexane.

Yield: 435 mg (79%), yellowish solid. $^{13}$C NMR (DMSO-$d_6$) δ=19.8, 25.5 27.4, 29.2 (cycl. CH$_2$), 53.4 (NCH$_3$), 63.6 (CH$_2$—$\underline{C}$H), 118.7, 121.9, 123.1 (tert. aryl-C), 111.4, 131.5, 172.4 (quat. aryl-C), 163.2 (C=N).

EXAMPLE 4

(R,R)-N,N'-Bis(4-trimethylammoniumsalicylidene)-1,2-cyclohexanediamine dihydrobromide

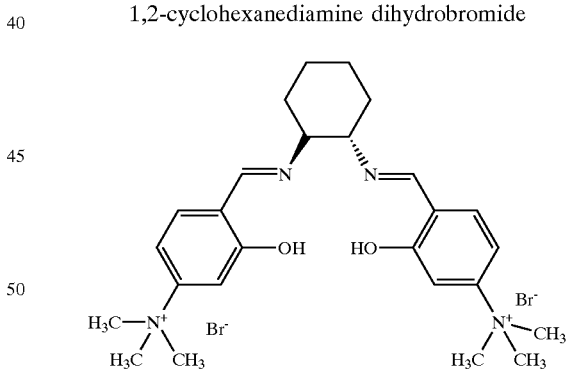

Synthesis and working up are carried out as in Example 1, starting from 500 mg (1.92 mmol) of 4-formyl-3-hydroxyphenyltrimethylammonium bromide and 0.105 g (0.915 mmol) of trans-1,2-diaminocyclohexane.

Yield: 299 mg (55%), yellowish-beige solid. $^{13}$C NMR (D$_2$O) δ=23.6, 29.5, 31.3, 33.1 (cycl. CH$_2$), 56.8 (NCH$_3$), 67.3 (CH$_2$—$\underline{C}$H), 107.5, 112.0, 136.1 (tert. aryl-C), 117.3, 152.4, 170.9 (quat. aryl-C), 166.6 (C=N).

EXAMPLE 5

N,N'-Bis(5-trimethylammoniumsalicylidene)-2-methylpropane-1,2-diamine dihydrobromide

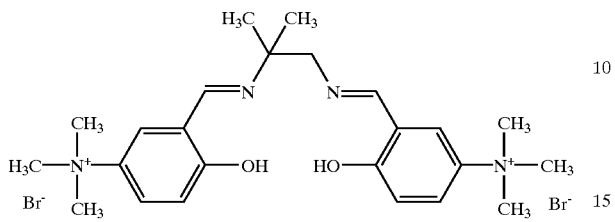

Synthesis and working up are carried out as in Example 1, starting from 500 mg (1.92 mmol) of 3-formyl-4-hydroxyphenyltrimethylammonium bromide and 81 mg (0.915 mmol) of 1,2-diamino-2-methylpropane.

Yield: 425.6 mg (81%), yellowish solid. $^{13}$C NMR (D$_2$O) δ=23.7 (CH$_3$), 57.3 (NCH$_3$), 60.0 ((CH$_3$)$_2$C), 64.2 (NCH$_2$), 119.7, 124.5, 125.7,135.2 (tert. aryl-C), 117, 137.2, 164.4 (quat. aryl-C), 164.5, 168.7 (C=N).

EXAMPLE 6

N,N'-Bis(5-trimethylammoniumsalicylidene)-2-methylpropane-1,2-diamine dihydrobromide

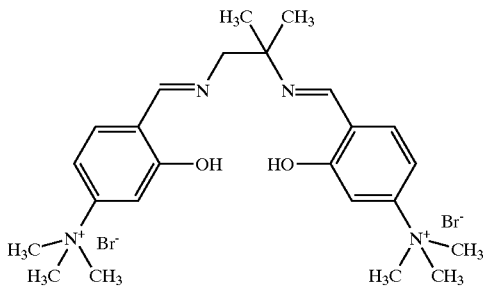

Synthesis and working up are carried out as in Example 1, starting from 500 mg (1.92 mmol) of 4-formyl-3-hydroxyphenyltrimethylammonium bromide and 81 mg (0.915 mmol) of 1,2-diamino-2-methylpropane.

Yield: 369 mg (70%), lemon-yellow solid. $^{13}$C NMR (DMSO-d$_6$) δ=24.8 (CH$_3$), 56.1 (NCH$_3$), 60.1 ((CH$_3$)$_2$—C), 67.9 (NCH$_2$), 109.5, 109.7, 109.8, 133.2, 133.6 (tert. aryl-C), 118.9, 150.0, 162.1, 163.2 (quat. aryl-C), 162.4, 166.4 (C=N).

EXAMPLE 7

4-(N-Ethyl-N-methylamino)salicylaldehyde

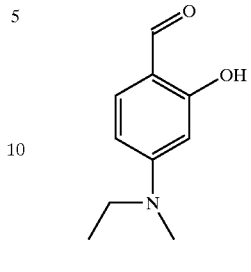

6.14 g (0.066 mol) of phosphorus oxychloride are cautiously added to 19 ml of dry DMF at −5° C. within a period of 5 minutes, during the course of which the temperature of the reaction solution should not exceed 10° C. Subsequently, a solution of 9.9 g (0.066 mol) of 3-(N-ethyl-N-methylamino)phenol in 14 ml of dry DMF is added thereto within a period of 10 minutes, during the course of which the temperature of the reaction solution should not exceed 20° C. When the addition is complete, the reaction solution is heated for 2 hours at 90° C. and then immediately poured onto 100 g of ice. The crude mixture is stirred for 30 minutes. The reaction solution is extracted three times with 100 ml of chloroform. The combined organic phases are concentrated under a high vacuum. The oily residue which remains is purified by column chromatography on silica gel (eluant n-hexanelchloroform 95:5). Yield: 5.8 g (26%), colourless solid.

$^1$H NMR (CDCl$_3$) δ=1.19 (m, 3H, CH$_3$—CH$_2$), 3.03 (s, 3H, NCH$_3$), 3.45 (m, 2H, CH$_3$—CH$_2$), 6.08 (s, 1H, aryl-H), 6.29, 7.30 (m, each 1H, aryl-H), 9.05 (s, 1H, CH=O), 11.62 (s, 1H, OH). $^{13}$C NMR (CDCl$_3$) δ=11.8 (CH$_3$—CH$_2$), 37.7 (NCH$_3$), 46.8 (CH$_3$—CH$_2$), 97.0, 104.5, 135.3 (tert. aryl-C), 111.6, 155.2, 164.2 (quat. aryl-C), 192.1 (C=O).

EXAMPLE 8

4-(N-Isopropyl-N-methylamino)salicylaldehyde

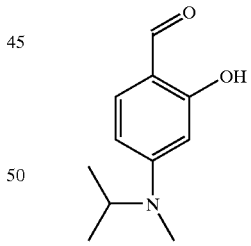

11 g (0.118 mol) of phosphorus oxychloride are cautiously added to 33 ml of dry DMF at −5° C. within a period of 5 minutes, during the course of which the temperature of the reaction solution should not exceed 10° C. Subsequently, a solution of 19.4 g (0.1176 mol) of 3-(N-isopropyl-N-methylamino)phenol in 25 ml of dry DMF is added thereto within a period of 10 minutes, during the course of which the temperature of the reaction solution should not exceed 20° C. When the addition is complete, the reaction solution is heated for 2 hours at 90° C. and then immediately poured onto 150 g of ice. The crude mixture is extracted three times with 100 ml of chloroform. The combined organic phases are concentrated under a high vacuum. The oily residue is purified by column chromatography on silica gel (eluant n-hexane/chloroform 95:5). Yield: 5.8 g (26%), colourless liquid.

$^1$H NMR (CDCl$_3$) δ=1.21 (m, 6H, (C$\underline{H}_3$)$_2$—CH), 2.87 (s, 3H, NCH$_3$), 4.18 (m, (CH$_3$)$_2$—C$\underline{H}$), 6.18 (s, 1H, aryl-H), 6.38, 7.27 (m, each 1H, aryl-H), 9.51 (s, 1H, C$\underline{H}$=O), 11.59 (s, 1H, OH). $^{13}$C NMR (CDCl$_3$) δ=19.7 ((C$\underline{H}_3$)$_2$CH), 30.1 (NCH$_3$), 48.6 ((CH$_3$)$_2$—C$\underline{H}$), 97.3, 104.8, 135.2 (tert. aryl-C), 111.6, 155.9, 164.3 (quat. aryl-C), 192.0 (C=O).

EXAMPLE 9

N,N'-Bis[4-(N-ethyl-N-methylamino)salicylidene]-1,2-ethylenediamine

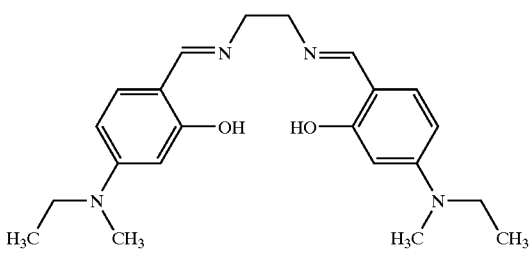

A solution of 80 mg (1.33 mmol) of ethylenediamine is added dropwise, at room temperature, to a solution of 500 mg (2.79 mmol) of 4-(N-ethyl-N-methylamino) salicylaldehyde and the reaction solution is heated for 4 hours at 70° C. After cooling to room temperature, the precipitate formed is filtered off, washed with a small amount of cold ethanol and dried in a vacuum drying cabinet at 30° C.

Yield: 476 mg (94%), yellow solid. $^1$H NMR (CDCl$_3$) δ=1.13 (m, 6H, C$\underline{H}_3$—CH$_2$), 2.92 (s, 6H, NCH$_3$), 3.38 (m, 4H, CH$_3$—C$\underline{H}_2$), 3.76 (s, 4H, NCH$_2$), 6.12 (m, 4H, aryl-H), 6.98 (m, 2H, aryl-H), 8.08 (s, 2H, C$\underline{H}$=N), 13.52 (s, br, 2H, OH). $^{13}$C NMR (CDCl$_3$) δ=11.7 (C$\underline{H}_3$—CH$_2$), 37.4 (NCH$_3$), 46.6 (CH$_3$—C$\underline{H}_2$), 58.4 (NCH$_2$), 68.8 (NC$\underline{H}_2$), 98.6, 103.3, 132.8 (tert. aryl-C), 108.6, 152.6, 165.4 (quat. aryl-C), 164.6 (C=N).

EXAMPLE 10

N,N'-Bis[4-(N-isopropyl-N-methylamino)salicylidene]-1,2-ethylenediamine

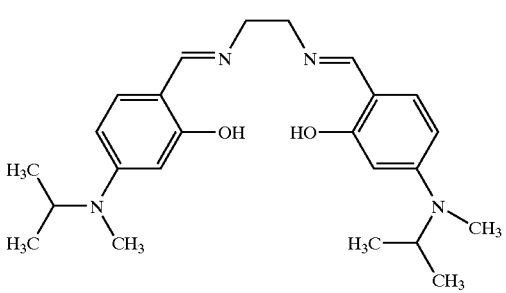

Synthesis and working up are carried out as in Example 9, starting from 500 mg (2.59 mmol) of 4-(N-isopropyl-N-methylamino)salicylaldehyde and 90 mg (1.5 mmol) of ethylenediamine.

Yield: 429 mg (81%), yellow solid. $^1$H NMR (CDCl$_3$) δ=1.17 (m, 12H, (C$\underline{H}_3$)$_2$—CH), 2.78 (s, 6H, NCH$_3$), 3.38 (m, 4H, CH$_3$—C$\underline{H}_2$), 3.74 (s, 4H, NCH$_2$), 4.12 (m, 2H, (CH$_3$)$_2$—C$\underline{H}$), 6.19 (m, 4H, aryl-H), 6.95 (m, 2H, aryl-H), 8.05 (s, 2H, C$\underline{H}$=N), 13.52 (s, br, 2H, OH). $^{13}$C NMR (CDCl$_3$) δ=19.6 (C$\underline{H}_3$—CH), 29.8 (NC$\underline{H}$—(CH$_3$)$_2$), 48.3 (NCH$_3$), 46.6 (CH$_3$—CH$_2$), 58.5 (NCH$_2$), 99.1, 103.7, 132.7 (tert. aryl-C), 108.7, 153.5, 165.2 (quat. aryl-C), 164.5 (C=N).

EXAMPLE 11

(R,R)N,N'-Bis[4-(N-isopropyl-N-methylamino)salicylidene]-1,2-cyclohexanediamine

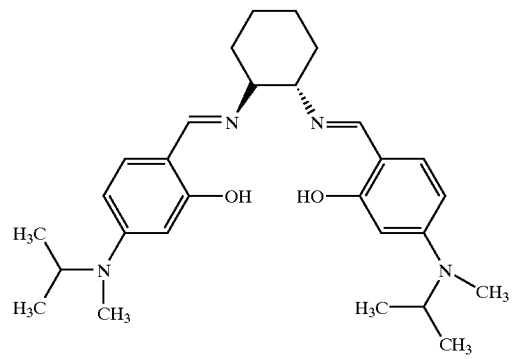

Synthesis and working up are carried out as in Example 9, starting from 500 mg (2.59 mmol) of 4-(N-isopropyl-N-methylamino)salicylaldehyde and 141 mg (1.23 mmol) of trans-1,2-cyclohexanediamine. Yield: 504 mg (88%), yellow solid.

$^1$H NMR (CDCl$_3$) δ=1.18 (m, 12H, (C$\underline{H}_3$)$_2$—CH), 1.41, 1.65, 1.83, 1.95 (m, each CH$_2$), 2.72 (s, 6H, NCH$_3$), 3.17 (m, 2H, cyc. CH), 4.10 (m, 2H, (CH$_3$)$_2$—C$\underline{H}$), 6.15 (m, 4H, aryl-H), 6.90 (m, 2H, aryl-H), 7.95 (s, 2H, C$\underline{H}$=N), 13.8 (s, 2H, OH). $^{13}$C NMR (CDCl$_3$) δ=19.6 (CH$_3$), 24.3, 33.2 (CH$_2$), 29.8 ((CH$_3$)—C$\underline{H}$), 48.2 (NCH$_3$), 71.0 (cycl. C$\underline{H}$), 99.2, 103.6, 103.8, 132.8 (tert. aryl-C), 108.7, 153.4, 165.5 (quat. aryl-C), 162.9 (C=N).

EXAMPLE 12

(R,R)-N,N'-Bis[4-(N-ethyl-N-methylamino)salicylidene]-1,2-cyclohexanediamine

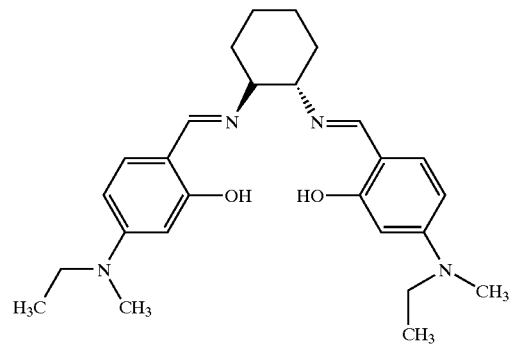

Synthesis and working up are carried out as in Example 9, starting from 500 mg (2.79 mmol) of 4-(N-ethyl-N-methylamino)salicylaldehyde and 152 mg (1.33 mmol) of trans-1,2-cyclohexanediamine. Yield: 569 mg (98%), yellow solid.

¹H NMR (CDCl₃) δ=1.10 (m, 6H, (C$\underline{H}_3$), 1.40, 1.61, 1.80, 1.93 (m, each 2H, CH₂), 2.88 (s, 6H, NCH₃), 3.10 (cycl. CH), 3.37 (m, 4H, NCH₂), 6.05 (m, 4H, aryl-H), 6.88 (m, 2H, aryl-H), 7.93 (m, 2H, C$\underline{H}$=N), 13.2 (s, br, 2H, OH). ¹³C NMR (CDCl₃) δ=11.6 (CH₃), 24.3, 33.2 (cycl. CH₂), 37.6 (NCH₃), 46.5 (CH₃$\underline{C}$H₂), 70.8 (cycl. $\underline{C}$H), 98.6, 103.2, 132.9 (tert. aryl-C), 108.5, 152.5, 165.9 (quat. aryl-C), 162.9 (C=N).

EXAMPLE 13

N,N'-Bis[4-(N-ethyl-N-methylamino)salicylidene]-2-methylpropane-1,2-diamine

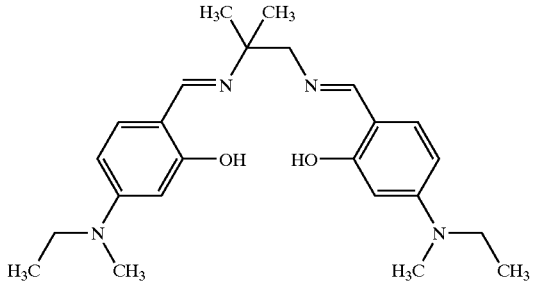

Synthesis and working up are carried out as in Example 9, starting from 500 mg (2.79 mmol) of 4-(ethylmethylamino)salicylaldehyde and 117 mg (1.33 mmol) of 1,2-diamino-2-methylpropane.

Yield: 518. mg (95%), yellowish solid. ¹³C NMR (CDCl₃) δ=11.7, 25.4 (CH₃), 37.5 (NCH₃), 46.6 (CH₃$\underline{C}$H₂), 58.6 ($\underline{C}$(CH₃)₂), 68.9 (NCH₂), 98.7, 99.1, 103.3, 133.0, 133.2 (tert. aryl-C), 108.6, 152.7, 153.0, 165.7, 167.8 (quat. aryl-C), 159.2, 164.7 (C=N).

EXAMPLE 14

N,N'-Bis[4-(N-isopropyl-N-methylamino)salicylidene]-2-methylpropane-1,2-diamine

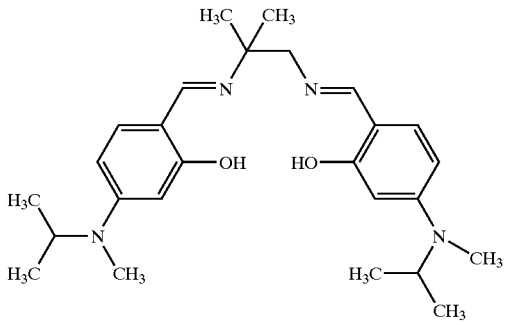

Synthesis and working up are carried out as in Example 9, starting from 500 mg (2.59 mmol) of 4-(N-isopropyl-N-methylamino)salicylaldehyde and 109 mg (1.23 mmol) of 1,2-diamino-2-methylpropane.

Yield: 524 mg (97%), yellowish oil. ¹³C NMR (CDCl₃) δ=19.7, 25.4, 29.8 (CH₃), 48.2 (NCH₃), 58.6 (N—$\underline{C}$(CH₃)₂—), 68.8 (N$\underline{C}$H₂), 99.1, 99.6, 103.7, 103.8, 132.8, 133.1 (tert. aryl-C), 108.7, 153.6, 153.9, 165.7, 167.8, (quat. aryl-C), 159.1, 164.6 (C=N).

EXAMPLE 15

N,N'-Bis(4-nitrosalicylidene)-1,2-ethylenediamine

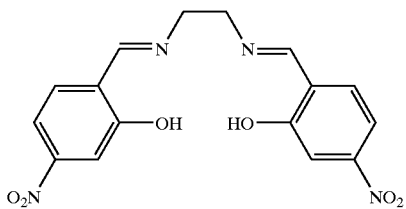

4 ml of methanol are added to a solution of 500 mg (2.99 mmol) of 4-nitrosalicylaldehyde (for preparation see Beilstein E IV, Vol. 8, 232) in 2 ml of ethanol. 95.2 mg (106 μl, 1.58 mmol) of ethylenediamine are added dropwise to the resulting yellow suspension. The reaction suspension is heated for 4 hours at 70° C. After cooling to room temperature, the precipitate formed is filtered off, washed with 2 ml of ethanol and dried to constant weight under a high vacuum at 30° C.

Yield: 488.1 mg, orange solid. ¹³C NMR (DMSO-d₆) δ=58.0 (NCH₂), 111.5, 123.3, 132.6 (tert. aryl-C), 149.5, 161.4 (quat. aryl-C), 165.6 (C=N).

The synthesis of the manganese(III)-salen complexes from the described salen ligands can be carried out in two ways: in known manner or in situ by the addition of Mn(II) salts in methanolic solution.

EXAMPLE 16

[(R,R)-N,N'-Bis(4-(N-isopropyl-N-methylamino)salicylidene)-1,2-cyclohexanediaminato]-manganese (III) chloride

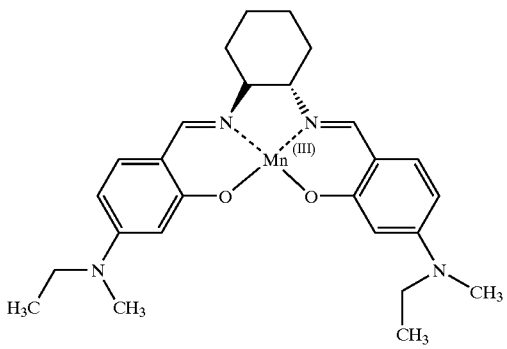

111 mg (0.452 mmol) of manganese(II) acetate tetrahydrate are added to a solution of 210 mg (0.452 mmol) of ligand from Example 11 in 9 ml of ethanol. The suspension is stirred for 8 hours at room temperature and then heated for 4 hours at 70° C. The resulting dark-red solution is concentrated under a high vacuum. The solid which remains is taken up in 9 ml of distilled water and 500 mg of sodium chloride are added. The precipitate formed is filtered off, washed with a small amount of cold water and dried under a high vacuum at 30° C.

Yield: 250 mg (quantitative), reddish-brown solid.

EXAMPLE 17

(R,R)-N,N'-Bis(5-(triethylammoniomethylsalicylidene)-1,2-cyclohexanediamine dihydrochloride

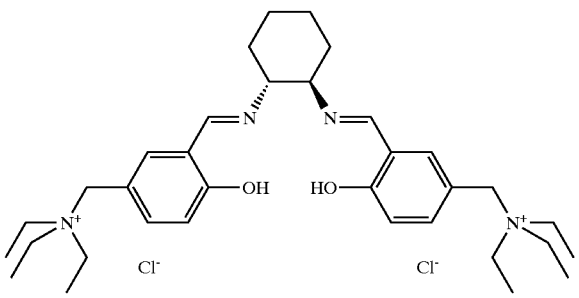

1.09 g (4 mmol) of (5-triethylammoniomethyl) salicylaldehyde chloride (for synthesis see T. Tanaka et al., Bull. Chem. Soc. Jpn. 1997, 70, 615–629) are dissolved in 10 ml of water and 0.228 g (2 mmol) of 1,2-diaminocyclohexane dissolved in 2 ml of water is added thereto. The yellow solution is stirred at room temperature for 2 hours and then concentrated at 60° C. bath temperature (10 mbar) using a rotary evaporator. 50 ml of tetrahydrofuran are added twice, followed each time by concentration. 1.22 g of the desired product are obtained in the form of yellow crystals of >90% purity (NMR).

$^{13}$C NMR (D$_2$O): δ=7.4 (CH$_3$), 23.8, 31.3, 52.3, 59.6 (aliph. CH$_2$), 67.7 (tert. C), 115.0, 116.5 (quat. aryl-C), 121.5, 138.5, 139.4 (tert. aryl-C), 166.9 (C=N), 171.5 (quat. aryl-C).

EXAMPLE 18

N,N'-Bis(5-(triethylammoniomethylsalicylidene)-1,2-ethanediamine dihydrochloride

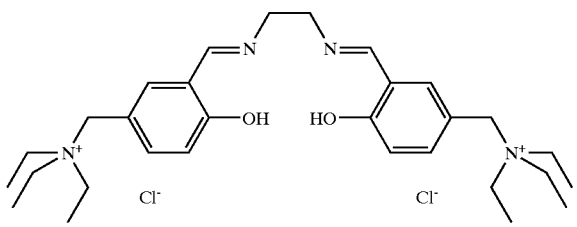

The compound is synthesised analogously to the directions given in Example 17. Yellow crystals of >90% purity (NMR) are obtained.

$^{13}$C NMR (D$_2$O) δ=7.4 (CH$_3$), 52.2, 53.5, 59.6 (in each case aliph. CH$_2$), 114.6,116.4 (quat. aryl-C), 120.5, 138.9, 139.6 (tert. aryl-C), 168.7 (C=N), 172.3 (quat. aryl-C).

EXAMPLE 19

Use of the Salen Complexes as DTI Catalysts

In order to examine the activity of the catalysts, the DTI activity is ascertained. The DTI (dye transfer inhibition) activity a is defined as the following percentage:

$$a=([Y(E)-Y(A)]/[Y(W)-Y(A)]) \times 100$$

wherein Y(W), Y(A) and Y(E) denote the CIE brightness values of the white material, of the material treated without the addition of catalyst and of the material treated with the addition of catalyst, in that order. a=0 denotes a completely unusable product, which when added to the washing liquor allows the dye transfer to proceed freely. a=100%, on the other hand, corresponds to a perfect catalyst, which completely prohibits staining of the white material by dye.

In order to ascertain the test data, the following test system is used: 7.5 g of white cotton fabric are treated in 80 ml of washing liquor. The liquor contains the standard washing agent ECE phosphate-free (456 IEC) EMPA, Switzerland, in a concentration of 7.5 g/l, 8.6 mmol/l H$_2$O$_2$ and a solution of the test dye. The washing process is carried out in a beaker in a LINITEST apparatus for 30 min. at 40° C. The catalyst is added in the concentration indicated in each case.

Commercially available Direct Brown 172 (dye 1) with 10 mg/l of the 250% formulation or Reactive Blue 238 (dye 2) with 6 mg/l of the 100% formulation are used as test dyes. The reflection spectra of the specimens are measured using a SPECTRAFLASH 2000 and converted by standard CIE procedure into brightness values (D65/10).

Table 1 shows the very good DTI effects a(%) of the complexes according to the invention. The concentration of catalysts used in the washing liquor is in each case 50 μmol/l (exception: the catalyst from Example 10: 15 μmol/l). The conditions of use are as described hereinabove.

TABLE 1

| Manganese complex of the ligands from Example | DTI effect a (%) | |
|---|---|---|
| | Dye 1 | Dye 2 |
| 1 | 89 | 90 |
| 2 | 93 | 88 |
| 3 | 88 | 92 |
| 4 | 91 | 92 |
| 5 | 84 | 89 |
| 6 | 87 | 93 |
| 9 | 91 | 94 |
| 10 | 88 | 90 |
| 11 | 86 | 89 |
| 12 | 87 | 85 |
| 13 | 85 | 85 |
| 14 | 88 | 87 |
| 15 | 89 | 91 |
| 16 | 90 | 85 |

EXAMPLE 20

Use of the Salen Complexes as Bleach Catalysts for Crockery

This Example illustrates the action of the manganese complexes of the ligands from Examples 3 and 6 as catalysts for peroxy compounds for cleaning tea-stained porcelain cups in an automatic dishwasher.

Staining Procedure

A tea brew (12 g of tea-leaves/liter) is prepared from black tea (Twinings brand) and hard water (total hardness: 18° dH) by stirring at 99° C. The tea brew is left to draw for five minutes and the tea is filtered. Approximately 100 ml of tea are then poured into a porcelain cup. The tea is left to stand in the cups for 30 minutes. The cups are then emptied in three steps each of approximately 35 ml. A period of five minutes is left between the emptying steps. The completely empty cups are dried for 60 minutes at 70° C.

Dishwashing Agent

A phosphate-containing base formulation (without oxygen bleaching agent and without TAED) having the following composition is used.

| Constituents | % by weight |
|---|---|
| sodium tripolyphosphate | 30–60 |
| sodium carbonate | 20–30 |
| hydrated 2.0 r silicate | 5–20 |
| non-ionic surfactant | 0.5–5 |
| protease | 0.5–5 |
| amylase | 0.5–5 |
| bentonite | 1–5 |

Cleaning Procedure

The cups are cleaned in a Miele G-690 D dishwasher on the delicate programme at 45° C. using hard water. In each cleaning programme 12 tea-stained cups are cleaned. The machine also contains six glasses with milk stains, 24 clean plates and 60 g of a mixture of various foodstuffs (for example spinach, egg, starch etc.). The dishwashing agent comprises: 17.2 g of the phosphate-containing base formulation, 1.72 g of sodium perborate-monohydrate, 0.8 g of TAED. As appropriate, 100 ppm of catalyst (ppm based on the metal) are added to the cleaning liquor. After the cleaning operation, the removal of the tea deposit is evaluated visually on a scale from 0 (=unchanged, very strong deposit) to 10 (=no deposit). Table 2 shows the ratings for our catalysts compared with a reference (TAED only no catalyst). The ratings indicated in Table 2 are the median values from several cleaning programmes each using 12 cups. The Table shows that the ratings for the catalysts according to the invention are significantly better than the reference value.

TABLE 2

Ratings for removal of the deposit

| Catalyst from Example | Rating |
|---|---|
| Reference (TAED only, no catalyst) | 1 |
| 3 | 7.5 |
| 6 | 8.5 |

What is claimed is:

1. A compound of formula

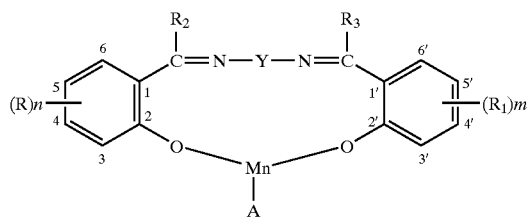

(1), wherein
n is 1 or 2,
m is 1 or 2,
A is an anion;
Y is a linear or branched alkylene radical of formula
—[C(R$_5$)$_2$]$_r$— wherein r is an integer of from 1 to 8 and the R$_5$ radicals are each independently of the others hydrogen or C$_1$–C$_4$alkyl; —CX═CX— wherein X is cyano, linear or branched C$_1$–C$_8$alkyl or di(linear or branched C$_1$–C$_8$alkyl)amino; —(CH$_2$)$_q$—NR$_4$—(CH$_2$)$_q$— wherein R$_4$ is hydrogen or C$_1$–C$_4$alkyl and q is 1, 2, 3 or 4; or
a 1,2-cyclohexylene radical of formula:

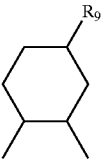

or a 1,2-aryl radical of formula

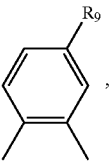

wherein R$_9$ is hydrogen, SO$_3$H, CH$_2$OH or CH$_2$NH$_2$,
R and R$_1$ are each independently of the other nitro, NR$_6$R$_7$ wherein R$_6$ is linear or branched C$_1$–C$_{12}$alkyl and R$_7$ is linear or branched C$_1$–C$_{12}$alkyl, with the proviso that R$_6$ and R$_7$ in the groups NR$_6$R$_7$ are not identical, or —CH$_2$—N$^\oplus$R$_4$R$_6$R$_7$ or —N$^\oplus$R$_4$R$_6$R$_7$ wherein R$_4$, R$_6$ and R$_7$ are as defined above, R$_2$ and R$_3$ are each independently of the other hydrogen, linear or branched C$_1$–C$_4$alkyl, unsubstituted aryl, or aryl substituted by cyano; by halogen; by OR$_5$ or COOR$_5$ wherein R$_5$ is hydrogen or linear or branched C$_1$–C$_4$alkyl; by nitro; by linear or branched C$_1$–C$_8$alkyl; by NHR$_6$ or NR$_6$R$_7$wherein R$_6$ and R$_7$ are identical or different and are each linear or branched C$_1$–C$_{12}$alkyl; by linear or branched C$_1$–C$_8$alkyl-R$_8$ wherein R$_8$ is a radical OR$_5$, COOR$_5$ or NR$_6$R$_7$ as defined above or is NH$_2$; or by —N$^\oplus$R$_4$R$_6$R$_7$ wherein R$_4$, R$_6$ and R$_7$ are as defined above,
and, when n and m are each 1, R$_2$ and R$_3$ are each hydrogen and Y is unsubstituted 1,2-cyclohexylene, R and R$_1$ are not each nitro in the 5- and 5'-position, respectively, and, when n and m are each 1, R$_2$ and R$_3$ are each hydrogen and Y is unsubstituted 1,2-ethylene, R and R$_1$ are not each N$^\oplus$(CH$_3$)(C$_2$H$_5$)$_2$ in the 4- and 4'-position, respectively.

2. A compound according to claim 1, wherein Y is a cyclohexylene radical, a radical of formula —(CH$_2$)$_r$— wherein r is an integer of from 1 to 4, or a radical of formula —C(R$_5$)$_2$—C(R$_5$)$_2$— wherein the R$_5$ radicals are each independently of the others hydrogen or methyl.

3. A compound according to claim 1, wherein the groups R and R$_1$ are in the 4- or 5-position of the respective benzene ring.

4. A compound according to claim 1, wherein the radicals R and R$_1$ are each nitro, NR$_6$R$_7$ in which R$_6$ and R$_7$ are each C$_1$–C$_4$alkyl, with the proviso that R$_6$ and R$_7$ are not identical, or —N$^\oplus$R$_4$R$_6$R$_7$ in which R$_4$, R$_6$ and R$_7$ are each C$_1$–C$_4$alkyl.

5. A compound according to claim 1, wherein the radicals R$_2$ and R$_3$ are each hydrogen, methyl, ethyl, or unsubstituted phenyl.

6. A compound according to claim 1, wherein the anion A is chloride, bromide, iodide or acetate.

7. A method of inhibiting the redeposition of migrating dyes present in a washing liquor, which comprises adding to the washing liquor, which comprises a peroxide-containing washing agent, from 0.5 to 150 mg of one or more compounds of formula (1) according to claim 1 per liter of washing liquor.

8. A washing agent containing
   I) from 5 to 90% A) of an anionic surfactant and/or B) of a non-ionic surfactant,
   II) from 5 to 70% C) of a builder substance,
   III) from 0.1 to 30% D) of a peroxide and
   IV) from 0.005 to 2% E) of a compound of formula (1) according to claim 1, the percentages in each case being percentages by weight, based on the total weight of the washing agent.

9. A cleaning agent for hard surfaces, comprising a compound of formula (1) according to claim 1 as bleach catalyst and a peroxy compound.

10. A cleaning agent for glazed tiles and floor tiles, or joints between such tiles, comprising a compound of formula (1) according to claim 1 as bleach catalyst and a peroxy compound and also, optionally, further additives.

11. A washing agent containing
   I) from 5 to 70% A) of an anionic surfactant and/or B) of a non-ionic surfactant,
   II) from 5 to 50% C) of a builder substance,
   III) from 1 to 12% D) of a peroxide and
   IV) from 0.02 to 1% E) of a compound of formula (1) according to claim 1, the percentages in each case being percentages by weight, based on the total weight of the washing agent.

12. A method to kill bacteria or to provide protection against attack by bacteria, which comprises contacting said bacteria with a solution containing a peroxy compound and a manganese complex of formula (1) according to claim 1 as catalyst for the reaction of the peroxy compound.

* * * * *